(12) United States Patent
Altman (10) Patent No.: US 8,388,581 B2
(45) Date of Patent: Mar. 5, 2013

(54) SYSTEM FOR TREATING THE HEART WITH POTENTIALLY EMBOLIC AGENTS THROUGH A RIGHT HEART APPROACH

(75) Inventor: Peter A. Altman, San Francisco, CA (US)

(73) Assignee: Biocardia, Inc., San Carlos, CA (US)

( * ) Notice: Subject to any disclaimer, the term of this patent is extended or adjusted under 35 U.S.C. 154(b) by 777 days.

(21) Appl. No.: 10/610,012

(22) Filed: Jun. 30, 2003

(65) Prior Publication Data

US 2004/0030286 A1 Feb. 12, 2004

Related U.S. Application Data

(63) Continuation of application No. 09/543,388, filed on Apr. 5, 2000, now Pat. No. 6,585,716.

(51) Int. Cl.
*A61M 5/178* (2006.01)
*A61M 29/00* (2006.01)

(52) U.S. Cl. .................. 604/164.1; 604/164.01; 606/194

(58) Field of Classification Search ............... 604/93.01, 604/96.01, 101.01, 101.02, 101.04, 164.01, 604/164.1, 164.11, 104, 915; 606/192, 194
See application file for complete search history.

(56) References Cited

U.S. PATENT DOCUMENTS

| | | | |
|---|---|---|---|
| 3,995,623 A | 12/1976 | Blake et al. .................. 128/2.06 |
| 4,689,041 A | 8/1987 | Corday et al. ................... 604/53 |
| 4,900,303 A | 2/1990 | Lemelson ........................ 604/54 |
| 5,244,460 A | 9/1993 | Unger et al. ..................... 604/53 |
| 5,354,279 A | 10/1994 | Hofling .......................... 604/164 |
| 5,464,395 A | 11/1995 | Faxon et al. ..................... 604/96 |
| 5,551,427 A | 9/1996 | Altman .......................... 128/642 |
| 5,655,548 A | 8/1997 | Nelson et al. .................. 128/898 |
| 5,711,298 A | 1/1998 | Littmann et al. ............... 128/642 |
| 5,766,152 A | 6/1998 | Morley et al. .................... 604/96 |
| 5,775,327 A | 7/1998 | Randolph et al. .............. 128/642 |
| 5,807,395 A | 9/1998 | Mulier et al. .................... 606/41 |
| 5,824,071 A | 10/1998 | Nelson et al. ...................... 623/3 |
| 5,830,222 A | 11/1998 | Makower ....................... 606/159 |
| 5,840,059 A | 11/1998 | March et al. ..................... 604/53 |
| 5,895,404 A | 4/1999 | Ruiz ............................. 606/185 |
| 5,913,842 A | 6/1999 | Boyd et al. ....................... 604/28 |
| 5,935,160 A | 8/1999 | Auricchio et al. ............. 607/122 |
| 5,951,585 A | 9/1999 | Cathcart et al. ............... 606/198 |
| 5,971,968 A | 10/1999 | Tu et al. ......................... 604/264 |
| 6,001,085 A | 12/1999 | Luric et al. .................... 604/282 |
| 6,004,295 A | 12/1999 | Langer et al. .................. 604/164 |
| 6,068,638 A | 5/2000 | Makower ....................... 606/159 |
| 6,071,292 A | 6/2000 | Makower et al. ............. 606/158 |
| 6,086,582 A | 7/2000 | Altman et al. ................... 606/41 |
| 6,102,887 A | 8/2000 | Altman ............................ 604/22 |
| 6,152,141 A | 11/2000 | Stevens et al. ................ 128/898 |
| 6,159,196 A | 12/2000 | Ruiz .............................. 604/500 |
| 6,159,225 A | 12/2000 | Makower ....................... 606/155 |
| 6,186,972 B1 | 2/2001 | Nelson et al. ...................... 604/8 |
| 6,190,353 B1 | 2/2001 | Makower et al. ............... 604/95 |
| 6,193,763 B1 * | 2/2001 | Mackin .......................... 600/427 |
| 6,217,554 B1 * | 4/2001 | Green ....................... 604/164.01 |
| 6,231,587 B1 | 5/2001 | Makower ....................... 606/198 |
| 6,283,951 B1 | 9/2001 | Flaherty et al. ............... 604/529 |
| 6,283,983 B1 | 9/2001 | Makower et al. ............. 606/198 |
| 6,346,098 B1 | 2/2002 | Yock et al. ..................... 604/508 |

(Continued)

*Primary Examiner* — Victoria P Shumate (74) *Attorney, Agent, or Firm* — K. David Crockett, Esq.; Crockett & Crockett, PC (57) ABSTRACT

Devices and methods are described for delivery of therapeutic substances to a depth within the heart muscle via the venous side of the heart, with a primary focus on delivery through the coronary sinus. The devices and methods may be combined with percutaneous access catheters in order to provide for right heart delivery of therapeutic agents.

27 Claims, 3 Drawing Sheets

U.S. PATENT DOCUMENTS

| | | | |
|---|---|---|---|
| 6,447,539 B1 | 9/2002 | Nelson et al. | 623/1.11 |
| 6,977,080 B1 * | 12/2005 | Donovan | 424/247.1 |
| 2002/0082392 A1 * | 6/2002 | Beach et al. | 530/387.3 |
| 2003/0007954 A1 * | 1/2003 | Naughton et al. | 424/93.7 |
| 2003/0078212 A1 * | 4/2003 | Li et al. | 514/22 |

* cited by examiner

SYSTEM FOR TREATING THE HEART WITH POTENTIALLY EMBOLIC AGENTS THROUGH A RIGHT HEART APPROACH

This application is a continuation of U.S. application Ser. No. 09/543,388, filed on Apr. 5, 2000, now U.S. Pat. No. 6,585,716.

FIELD OF THE INVENTIONS

The inventions described below relate to site specific delivery of therapeutic agents, structures and catheter systems to achieve site specific delivery of therapeutic agents, and means for implanting and using these systems to enable delivery of therapeutic agents to the body.

BACKGROUND OF THE INVENTIONS

The devices and methods described in this application provide for safer and better treatment of various forms of heart disease. The forms of heart disease which may be treated with these devices and methods include angina pectoris and related causes such as ischemia, arrhythmia, stenosis and restenosis. Other conditions such as chronic heart failure, heart transplant infection and rejection can be treated. Each of these conditions involves regions of tissue which are diseased, and these diseased regions of the heart may be treated with various therapeutic agents.

Ischemia and myocardial infarct are two important cardiac disease states. Symptoms are those included in the constellation of symptoms referred to as angina pectoris, and include constricting pain in the chest and radiating pain in the arms. Ischemic tissue is tissue which is starved of oxygen and nutrients, usually because the tissue is not receiving adequate blood supply. It is characterized by limited metabolic processes which causes poor functionality, and may lead to fibrillation and death. In turn this hinders the normal functioning of the heart cells or myocytes in an ischemic region. Ischemia is reversible, such that cells may return to normal function once they receive the proper nutrients. If an ischemic, or damaged, region of the heart does not receive enough nutrients to sustain the myocytes they are said to die, and the tissue is said to become infarcted. Infarcted tissue may also lead to fibrillation and death, and infarction is irreversible. The onset of ischemia and infarction are often referred to as a heart attack.

A number of methods have been developed to treat ischemic regions in the heart. Systemic delivery of anti-ischemic agents such as nitrates or vasodilators reduces vascular resistance, thereby reducing the amount of work the heart must perform, which in turn allows the heart function properly even with reduced blood flow. These drugs are taken orally or by injection, and affect the entire body as well as the ischemic tissue. Ischemic tissue caused by clogged arteries or vascular obstructions are treated by removal of the vascular obstruction. This can be done with the systemic delivery of pharmacological agents such as TPA, urokinase, or anti-thrombolytics which can break up the obstruction. It can also be done with catheter based techniques intended to open clogged arteries and remove the vascular obstructions. These catheter-based techniques include percutaneous transluminal coronary angioplasty (PTCA), atherectomy, and stent placement. These techniques can increase myocardial blood flow (perfusion), thereby providing the heart with sufficient oxygen and nutrients. More drastic but very reliable procedures such as coronary artery bypass surgery can also be performed.

Recently, some references have proposed injection of therapeutic agents into myocardium through the coronary arteries. Unger, et al., *Method To Foster Myocardial Blood Vessel Growth And Improve Blood Flow To The Heart*, U.S. Pat. No. 5,244,460 (Sep. 14, 1993) proposed injection of angiogenic growth factors into the coronary arteries through a catheter, with the intention that the growth factors be perfused along with the blood flow into the myocardium. This approach is problematic because (1) all the tissue served by the coronary artery is supplied with angiogenic agent, even though only the region of artery including the occlusion and downstream regions requires the angiogenic agent and (2) to ensure adequate supply to the ischemic area, substantially more angiogenic growth factor than is needed to treat the ischemic area must be delivered to the coronary artery. This may be substantially more tissue than is in need of local drug delivery therapy. The growth factors will act in the tissue which the coronary arteries successfully perfuse. The excess growth factors may cause unwanted angiogenesis in tissue elsewhere in the body. The cornea is described by Unger as such a location, but perhaps more critical is inappropriate delivery of these factors to the brain. Additionally, placement of delivery devices within the coronary arteries as Unger describes will tend to obstruct these arteries and may augment occlusive thrombosis formation. There is a significant need for a means and method of minimizing the amount of growth factors for introducing angiogenesis by delivering these agents only to the site where they are most needed.

Several other cardiac disease states are related to the diseases already discussed. After stent placement, and after opening vessels using balloon angioplasty (PTCA), the vessels often lose patency over time. This loss of patency due to restenosis may be reduced by appropriate pharmacological therapy in the region of the artery. These problems have not been resolved, and current proposals included irradiating the blood vessel in the region of the balloon angioplasty or stent. Cardiac arrhythmias are abnormal rhythmic contractions of the myocardial muscle, often introduced by electrical abnormalities, or irregularities in the heart tissue. Arrhythmias arise from arrhythmogenic tissue, sometimes including a focal point referred to as the focus of the arrhythmia. Arrhythmogenic tissue is sometimes caused by ischemia and infarct, and is sometimes causes by other conditions such as an inherent defect in the heart. Arrhythmogenic tissue may also be treated by injection of therapeutic agents, injected in the same manner as is used to treat ischemia and infarct.

Local drug delivery provides many advantages. Approaches for local delivery of agents at a depth within a tissue enables the delivery of drugs to sites where they are most needed, reduces the amount of drugs required, increases the therapeutic index of the particular dosing regime, and increases the control over the time course of agent delivery. These, in turn, improve the viability of the drugs, lower the amount (and cost) of agents, reduce systemic effects, reduce the chance of drug-drug interactions, lower the risk to patients, and allow the physician to more precisely control the effects induced. Such local delivery may mimic endogenous modes of release, and address the issues of agent toxicity and short half lives. March, U.S. Pat. No. 5,840,059 describes a means of delivering therapeutic agents into a channel within the heart, but suffers the serious limitation in that the material will likely not be retained in the channels. The viscous carrier suggested by March to help retain the material within the channels poses substantial risk as embolic material should it escape from the channels and be released into the endocardial chamber. Our own applications have provided devices, methods, and formulations of therapeutic agents for use in treating various cardiac diseases. These applications have disclosed percutaneous delivery of therapeutic agents to the heart through the arterial system and the left heart, with devices and methods to enhance the retention of therapeutic agents within the heart wall.

SUMMARY

The devices and methods described below provide for delivery of therapeutic substances to a depth within the heart muscle via the venous side of the heart, with a primary focus on delivery through the coronary sinus and through the right ventricular apex and septum. The devices and methods may be combined with percutaneous access catheters in order to provide for right heart delivery of therapeutic agents. The devices and methods may be combined with permanently implantable devices with and without the electrical sensing and stimulation capabilities, and they provide either sustained delivery of therapeutic agents locally over time via a fluid pathway, or may deliver fluid agents upon demand as a result of an event sensed by a patient are described. Devices and techniques for delivering drug microformulations such as microspheres and liposomes, and drug delivery structures from an acute use catheter system are also described.

DETAILED DESCRIPTION OF THE INVENTIONS

Figure 1:
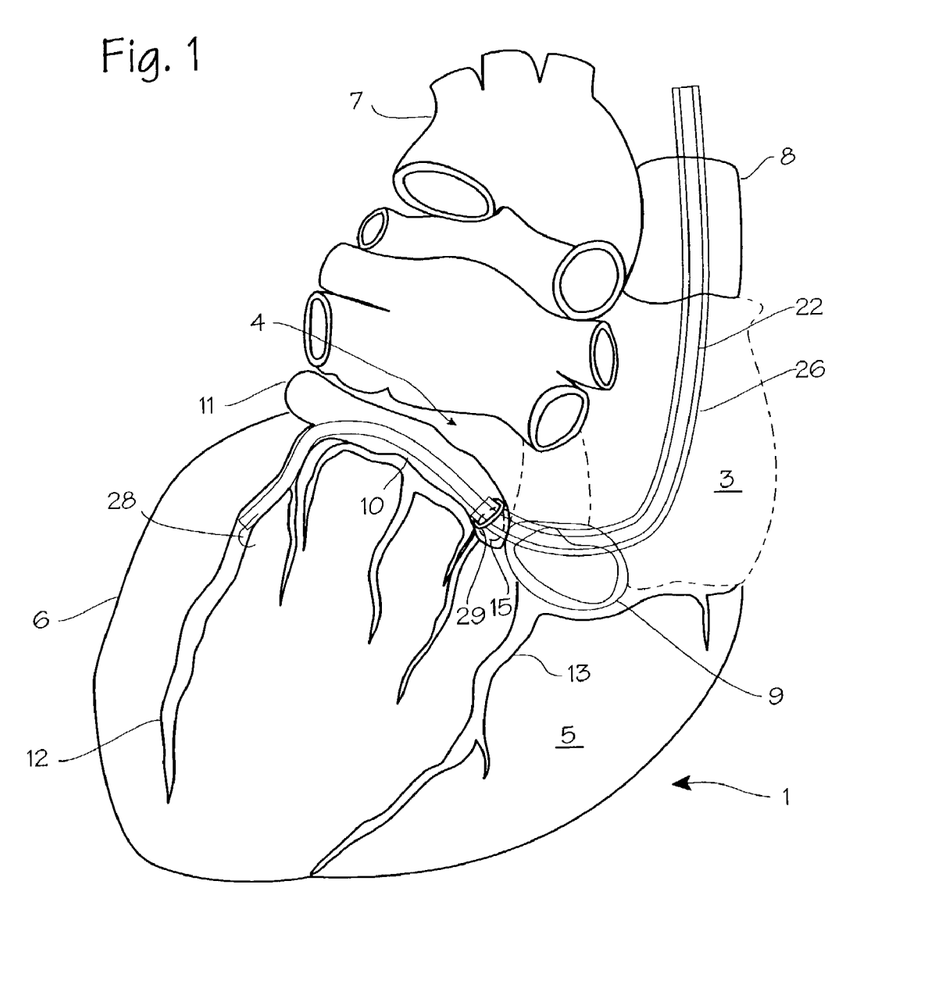
FIG. 1 is an illustration of the method of treating the human heart.

FIG. 1 illustrates the method of treating the human heart. The heart 1 of the patient is illustrated in a posterior view. The heart comprises the four chambers, the right atrium 3, the left atrium 4, the right ventricle 5 (hidden behind the pulmonary veins in this view) and the left ventricle 6. The left ventricle is the chamber that pumps blood out of the heart to the test of the body through the aorta 7. The right atrium collects venous blood from that superior vena cava 8 and the inferior vena cava 9, and also from the coronary sinus 10. The coronary sinus in turn collects blood from the great cardiac vein 11, the posterior vein of the left ventricle 12, the middle cardiac vein 13, and the anterior cardiac vein 14 (shown in phantom). The coronary sinus is joined to the right atrium through an aperture called the coronary ostium 15. The ostium is covered by a valve which is not shown.

Catheter based procedures for treating the heart, in which therapeutic agents are injected into the heart, may be directed toward any chamber of the heart. When catheters are placed in the left ventricle and foreign materials are injected into the left ventricle, two detrimental effects may occur: first, due to the high blood flow in the left ventricular chamber, the therapeutic agents injected are quickly washed away into the blood stream and delivered to the rest of the body, raising systemic levels of the therapeutic agents and increasing the dosage required to create the desired local effect in the ventricle wall; and second, releasing or creating potentially embolic or thrombogenic material into the blood stream and creating a risk of stroke should emboli reach the brain. When catheters are placed in the right ventricle 5 or right atrium 3, or foreign materials are injected into these chambers, any emboli created is pumped with the blood into the lungs to be filtered or lodged in the lungs with little effect.

Our co-pending U.S. application Ser. No. 09/407,461 filed Sep. 28, 1999 describes several therapeutic agents useful for local delivery into the heart, including macromolecule and microsphere formulations of anti-restenosis agents and angiogenic agents into the heart wall. Each of these therapeutic agents (and others) can be delivered through the right heart delivery pathway described here. Referring again to FIG. 1, the drug delivery catheter 22 has been inserted into the venous portion of the patient's vasculature so that the distal end 23 of the catheter enters into either the inferior vena cava, as shown, or the superior vena cava and the distal tip 24 of the catheter enters the great cardiac vein 11 and, as shown, extends into the posterior vein of the left ventricle (item 12). A guide catheter 26 has been used to guide the drug delivery catheter, and extend until the distal tip 27 extends into the vena cava and the coronary sinus. The catheter distal tip 24 includes a penetrating element 28, for example a curved or helical needle, which is selectively extended from the distal tip and is forced through the wall of the vein, and into the myocardium. Therapeutic agents are then injected into the myocardium through the catheter and needle.

To enhance the retention of the therapeutic agents in the needle track and/or within the myocardium in the face of natural fluid flow from the myocardium into the vein, the venous flow path is shut off by occluding the coronary ostium 10 with the guide catheter which has occluding mechanism 29 (visible in FIG. 2) located near its distal end. The occluding mechanism may be a flange, a collar or other circumferential projection on a portion of the guide catheter 26 just proximal to the distal tip 27 of the guide catheter, and may be formed with a circumferential balloon which is inflated once the catheter is in place, or it may be formed merely of a low durometer annular projection which is soft enough to be deformed during passage through the ostium. (The occluding mechanism could also be the guide catheter distal tip itself, if it of sufficient diameter to substantially occlude the ostium as may be the case with very small patients). The drug delivery catheter and the guide catheter are longitudinally slidable relative to each other, so that the flange may be moved longitudinally relative to the distal tip 23 and penetrating element of the drug delivery catheter, so that the collar may occlude the ostium while the drug delivery catheter can reach various points within the coronary sinus and cardiac veins. With the collar placed in occluding position relative to the coronary ostium, venous flow into the cardiac vein is temporarily stopped, so that therapeutic agents injected through the cardiac vein and into the myocardium is not flushed backwardly by the normal flow of venous blood.

Figure 2:
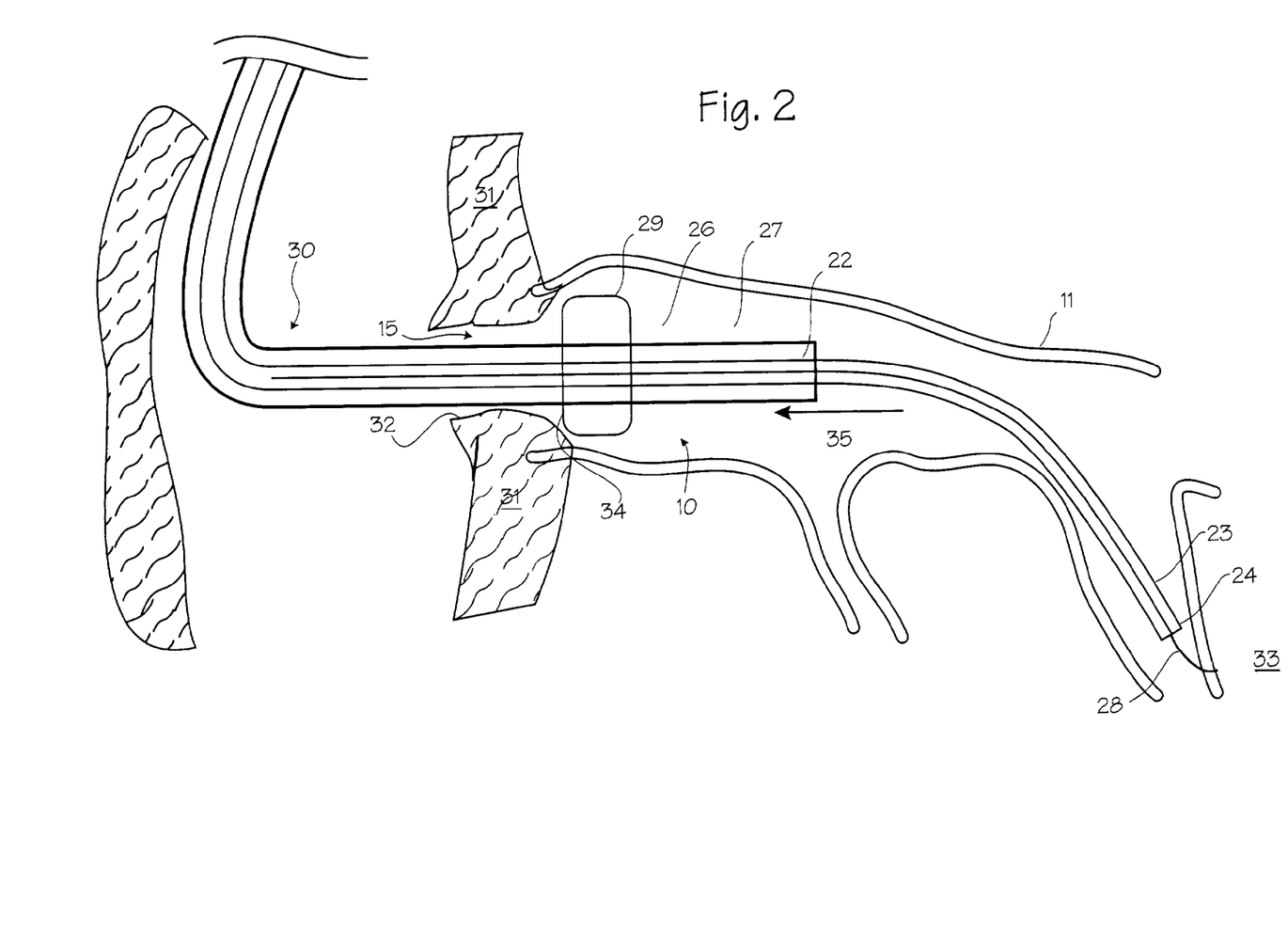
FIG. 2 is an illustration of the system for treating the human heart according to the method illustrated in FIG. 1.

The relationship of the collar to the ostium is more clearly illustrated in FIG. 2, which shows the intra-cardiac portion 30 of the drug delivery catheter 22 and the associated cardiac structures including the atrial ostial wall 31, the atrial ostium (the hole indicated by item 15) and the valve 32. The catheter distal tip 24 of the drug delivery catheter 22 lies within the cardiac venous system, for example the anterior section of the great cardiac vein 11 feed into the coronary sinus 10. The penetrating element is proximate the target site 33, which is the area of tissue which the surgeon intends to treat. The guide catheter, disposed coaxially over the drug delivery catheter, is advanced so that the distal tip of the guide catheter protrudes into the coronary sinus and the flange lies just distal (relative to the catheter) to the coronary ostium. (The relationship need not be strictly coaxial; it is sufficient that the two parts may slide along the same longitudinal axis, and they need not be centered on the same axis). Where the flange is provided in the form of an expandable balloon, the balloon is expanded to occlude the coronary ostium and block the flow of venous blood from the coronary sinus into the right atrium. Where the flange is provided in the form of a resilient flange, it merely compresses to slip through the ostium in either direction. The longitudinal distance between the distal end of the drug delivery catheter and the proximal face 34 of the occluding mechanism 29 approximates the expected length coronary venous pathway between the ostium and the target site 33 of cardiac tissue. Preferably, the drug delivery catheter is slidably disposed within the guide catheter so that it may be moved longitudinally within the guide catheter to reach various target sites within the coronary venous system while the occluding mechanism of the guide catheter remains in its occluding position relative to the ostium. Venous blood flow is in the direction of arrow 35, which would tend to resist injection of fluid in the retrograde direction.

To use the drug delivery catheter system, the guide catheter and drug delivery catheter are inserted into the patient's venous system and navigated to the superior or inferior vena cava. The distal end of the catheter system is then passed retrograde through the coronary ostium and into the coronary sinus, and the drug delivery catheter distal tip is navigated to the target site within the coronary venous system. The delivery can be accomplished percutaneously for acute applications or operating room procedures, such as supply of a small number of injections in short order, as in response to a heart attack or other acute condition, or in-hospital treatment of chronic conditions. Placement of the drug delivery catheter can also be accomplished surgically (open or minimally invasive surgery) along with internal placement of a drug reservoir and pump, for automatic or chronic supply of therapeutic agents to the heart on an ongoing basis. In any case, once the penetrating element is forced through the wall of the vein and into the myocardium, drug delivery can be initiated. The occluding mechanism is placed over the ostium (and expanded) to occlude the ostium, and drug delivery is initiated. Drug delivery is accomplished by injection therapeutic agents through a lumen extending from the proximal end of the drug delivery catheter to the penetration element. The occluding mechanism may be removed or contracted, and the penetrating element may be left in place or moved, depending on the desired course of injections. Additionally, the penetrating element may be comprised of, or coated with, therapeutic agents, so that therapeutic agents are delivered upon penetration and/or bio-erosion of the penetrating element, and in this-case, fluid injection through the drug delivery catheter will be unnecessary.

Many drugs and other therapeutic agents may be used in the procedure. For treatment of ischemic heart disease, therapeutic agents such as VEGF-121, VEGF-165, VEDF-145, VEGF-189, aFGF, bFGF (or gene therapy preparations of these agents) may be used, either in freely available formulations or time-release formulations. To treat congestive heart failure, therapeutic agents such as Natrecor® (nesiritide), the recombinant form of B-type natriuretic peptide (BNP). To enhance retention of the therapeutic agents in the needle track and/or within the myocardium, the needle may be left in place for several seconds, and the therapeutic agents slowly injected at a rate of about 0.1 milliliters per minute. The devices and methods described below provide for delivery of therapeutic substances to a depth within the heart muscle via the venous side of the heart. The devices and methods may be combined with percutaneous access catheters in order to provide for right heart delivery of therapeutic agents. The devices and methods may be combined with permanently implantable devices with and without the electrical sensing and stimulation capabilities, and they provide either sustained delivery of therapeutic agents locally over time via a fluid pathway, or they may deliver fluid agents upon demand as a result of an event sensed by a patient are described. The devices and techniques may be used for delivering drug microformulations such as microspheres and liposomes, and drug delivery structures from an acute use catheter.

Controlled release matrices proposed for use elsewhere in the body include polymeric matrices, hydro gels, fibrin glues, and the like to provide for sustained release of a drug over time to the body. Microsphere structures such as those provided as Alkermes Prolease system are one example of polymeric matrices. Implantation of these controlled release structures creates a high potential to for embolic events, as they can aggregate and migrate from the heart and travel to the brain and other organs. When microspheres are delivered in to the body at sited where they can enter arteries supplying the brain, doses of microspheres in the size range of 10 to 50 um are limited to 50,000 microspheres. Similar doses of 99TC labeled macro aggregated albumin particles are used to assay right to left shunting in pediatric cardiology. These 99TC spheres provide extremely small volumes for drug delivery, but increasing the diameter of the spheres or their number may cause embolisms should they be delivered into the left heart chambers inadvertently. Similar problems exist for gel based controlled release systems. The solution to date has been limitation of the size of molecules and particles in the therapeutic agent, and limitation of the dose or total amount injected at any one time. Intramyocardial access for such controlled release systems through the venous side of the heart eliminates the possibility that embolic events could occur in the arteries of the body. Thus, even if a large portion of the injected microspheres wash out of the delivery site during and after injection due to poor techniques or poor formulation of the microspheres, there would be little chance of embolic events. This approach also makes a great deal of sense if placing an indwelling implant for infusing the left ventricle myocardium through a fluidic pathway with potentially embolic therapeutic agents.

Figure 3:
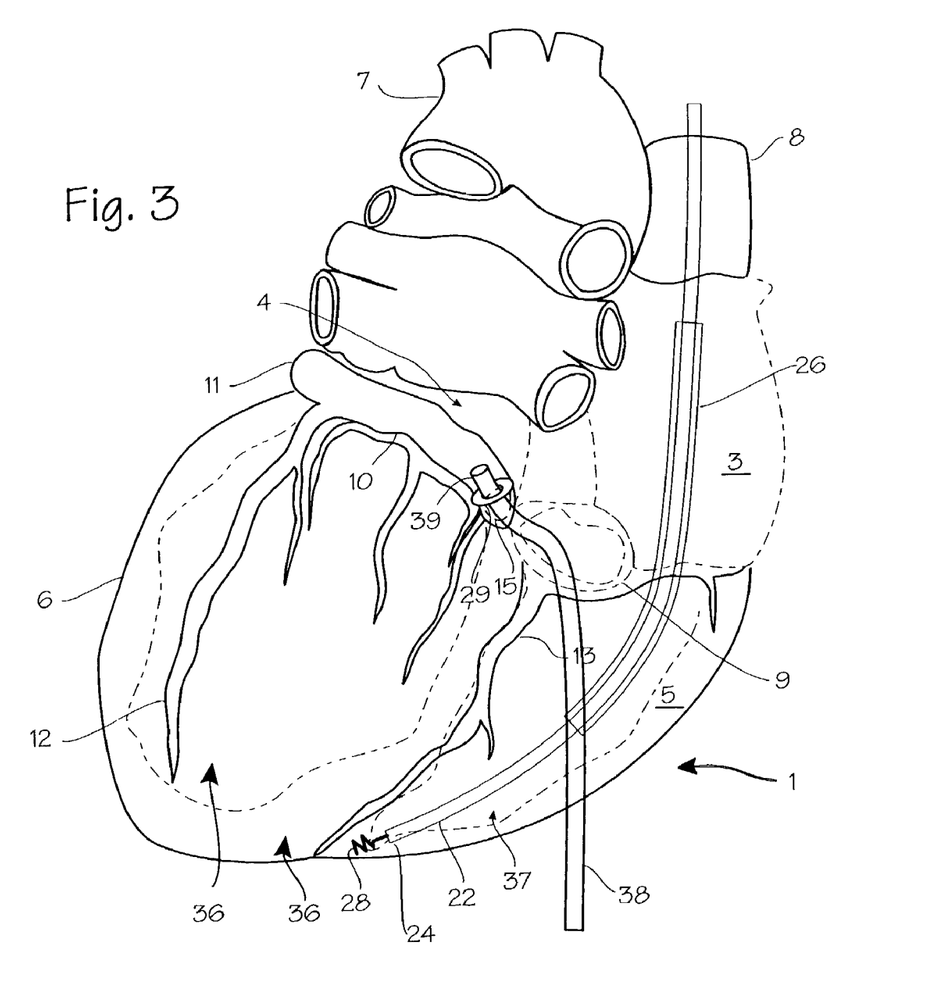
FIG. 3 is an illustration of the method of treating the human heart.

FIG. 3 illustrates another method of right heart access for treatment of the apex region of the heart. This may be used to deliver therapeutic agents to the apex of the right ventricle, the apex of the left ventricle, or to the coronary septum. A drug delivery catheter 22 is shown in use to deliver therapeutic agents to the coronary septum and the apex of the heart, in particular the apical section of the right ventricle. The catheter distal tip 24 of the drug delivery catheter 22 is shown in the proximity of the apex 36 of the heart, and the penetrating element has penetrated the myocardium from the inside of the right ventricular chamber 37. The drug delivery catheter has been navigated through the patient's venous system, into the superior vena cava (approach may also be made through the inferior vena cava), through the right atrium and finally into the right ventricle. With the delivery catheter 22 in place, an ostium occlusion catheter 38 is also inserted percutaneously and navigated through the venous system so that the distal tip 39 of the occlusion catheter is passed through the coronary ostium, and the occluding mechanism is in occluding relationship with the coronary ostium. The occlusion catheter may be routed through a common guide catheter with the drug delivery catheter (and hence inserted through the same percutaneous access point) or it may be delivered through a separation guide catheter, as shown, which is routed through the inferior vena cava to reach the right atrium. The surgeon operates the occluding mechanism to cause it to expand and occlude coronary ostium. (With the ostium occluded, venous flow within the entire heart in impeded.) With the ostium occluded, the surgeon injects a therapeutic agent through the drug delivery catheter into the myocardium. Therapeutic agents may be injected slowly and over an intra-operative time frame of several minutes to several hours.

The approach illustrated in FIG. 3 can be used for injections elsewhere in the heart, either through endocardial approaches, open epicardial approaches, or minimally invasive epicardial approaches. The ostium occlusion can also be used in conjunction with injections of therapeutic agents through the coronary arteries. For example, the drug delivery catheter may be delivered percutaneously into the left ventricle chamber 40. When intramyocardial delivery to the ventricles is performed by either an endocardial intraventricular approach or other routes, much of the washout is identified in the venous outflow of the heart. Obstructing this venous outflow forces agents to be retained for greater periods of time within the heart. Particularly for heparin binding agents such as bFGF and VEGF-165 which bind to heparin sulfate proteoglycans, an increased residence time in the tissue should increases their retention in the tissue over even longer times. Obstructing their egress from the injection site by occluding the coronary sinus for the first one to five minutes after injection will increase their residence time for binding, and increase their longer-term retention well after the obstruction is removed. This may be combined with any approach for cardiac delivery, but is preferred for intramyocardial (through coronary sinus, trans-endocardial, or trans-epicardial routes) delivery and intracoronary delivery.

The devices and methods described above also enable treatment of the left ventricle by placing agents in the right ventricular walls. Intramyocardial placement of delivery systems in the right side of the heart may be performed such that the left side of the heart is exposed to the therapeutic agents delivered. Such systems may be implanted into the shared ventricular septum or the right ventricular apex to optimize their effects on the left heart. Appropriate therapies to be delivered to the apex or the septum may include angiogenic agents, anti-restenosis agents, and agents for the treatment of chronic heart failure. These may be provided in a controlled release form without fear of embolic events. This is particularly useful for implantable transient on-demand delivery systems (for acute treatments) which deliver small molecule therapeutics as well as sustained release systems as described above. Implantable systems for on-demand delivery for the ventricular septum may include the matrices or reservoirs of antiarrhythmic agents for the termination of ventricular tachyarrhythmias.

While the preferred embodiments of the devices and methods have been described in reference to the environment in which they were developed, they are merely illustrative of the principles of the inventions. Other embodiments and configurations maybe devised without departing from the spirit of the inventions and the scope of the appended claims.

I claim:

1. A system for treating the heart by injecting therapeutic agents into a target site within the coronary venous system, said system comprising:
a device comprising:
a drug delivery catheter having a proximal end and a distal end, said drug delivery catheter having a penetrating drug delivery element disposed on the distal end and a drug delivery lumen extending from the proximal end to the distal end of said drug delivery catheter;
an occluding mechanism disposed about the drug delivery catheter a short distance proximal to the penetrating element, said occluding mechanism adapted to occlude the ostium of the coronary sinus when placed in proximity thereto; and
a reservoir; and
a potentially embolic therapeutic agent comprising an implantable matrix contained within the reservoir, said reservoir in communication with the drug delivery lumen.

2. The system of claim 1 wherein the occluding mechanism is further characterized by a proximal face and wherein the proximal face of the occluding mechanism is adapted to occlude the ostium of the coronary sinus.

3. The system of 2 wherein the distance between the penetrating element and the proximal face of the occluding mechanism approximates the expected length of the coronary venous system between the ostium and the target site of cardiac tissue.

4. The system of claim 1 wherein the occluding mechanism is an inflatable balloon.

5. The system of claim 4 wherein the balloon is characterized by a proximal face and wherein the proximal face of the balloon is adapted to occlude the ostium of the coronary sinus.

6. The system of claim 5 wherein the distance between the penetrating element and the proximal face of the balloon approximates the expected length of the coronary venous system between the ostium and the target site of cardiac tissue.

7. The system of claim 1 wherein the short distance between the penetrating element and the occluding mechanism approximates the expected length of the coronary venous system between the ostium and the target site of cardiac tissue.

8. The system of claim 1, wherein the target site is within the posterior vein of the left ventricle.

9. The system of claim 1 wherein the therapeutic agent further comprises VEGF.

10. The system of claim 1 wherein the therapeutic agent further comprises an angiogenic agent.

11. The system of claim 1 wherein the therapeutic agent further comprises an anti-restenosis agent.

12. The system of claim 1 wherein the short distance is sufficient to place the occluding mechanism in occluding relationship to the ostium of the coronary sinus while placing the penetrating element at the target site.

13. A system for treating the heart by injecting therapeutic agents into a target site within the coronary venous system, said system comprising:
a device comprising:
a drug delivery catheter having a proximal end and a distal end, said drug delivery catheter having a penetrating drug delivery element disposed on the distal end and a drug delivery lumen extending from the proximal end to the distal end of said drug delivery catheter;
a guide catheter slidably disposed about the drug delivery catheter, said guide catheter having a proximal end and a distal end, said distal end of the guide catheter adapted for insertion into the coronary sinus;
an occluding mechanism disposed about the guide catheter, said occluding mechanism adapted to occlude the ostium of the coronary sinus; and
a reservoir; and
a potentially embolic therapeutic agent comprising an implantable matrix contained within the reservoir, said reservoir in communication with the drug delivery lumen.

14. The system of claim 13 wherein the therapeutic agent further comprises VEGF.

15. The system of claim 13 wherein the therapeutic agent further comprises an angiogenic agent.

16. The system of claim 13 wherein the therapeutic agent further comprises an anti-restenosis agent.

17. The system of claim 13 wherein the distance between the penetrating element and the occluding element is adjustable to permit movement of the penetrating element within the coronary venous system while the occluding mechanism is in proximity to the ostium of the coronary sinus.

18. The system of claim 13 wherein the distance between the penetrating element and the occluding element approximates the expected length of the coronary venous system between the ostium and the target site of cardiac tissue.

19. The system of claim 13, wherein the occluding mechanism is an inflatable balloon, and wherein the distance between the penetrating element and the proximal face of the balloon approximates the expected length of the coronary venous system between the ostium and the target site of cardiac tissue.

20. A system for treating the heart by injecting therapeutic agents into a target site within the coronary venous system, said system comprising:
a device comprising:
a drug delivery catheter having a proximal end and a distal end, said drug delivery catheter having a penetrating drug delivery element disposed on the distal end and a drug delivery lumen extending from the proximal end to the distal end of said drug delivery catheter;
an occluding mechanism disposed about the drug delivery catheter a short distance proximal to the penetrating element, said occluding mechanism adapted to occlude the ostium of the coronary sinus when placed in proximity thereto; and
a reservoir; and
a potentially embolic therapeutic agent comprising an implantable controlled release matrix comprising a polymeric matrix contained within the reservoir, said reservoir in communication with the drug delivery lumen.

21. A system for treating the heart by injecting therapeutic agents into a target site within the coronary venous system, said system comprising:
a device comprising:
a drug delivery catheter having a proximal end and a distal end, said drug delivery catheter having a penetrating drug delivery element disposed on the distal end and a drug delivery lumen extending from the proximal end to the distal end of said drug delivery catheter;
an occluding mechanism disposed about the drug delivery catheter a short distance proximal to the penetrating element, said occluding mechanism adapted to occlude the ostium of the coronary sinus when placed in proximity thereto; and
a reservoir; and
a potentially embolic therapeutic agent comprising an implantable controlled release matrix comprising a hydrogel contained within the reservoir, said reservoir in communication with the drug delivery lumen.

22. A system for treating the heart by injecting therapeutic agents into a target site within the coronary venous system, said system comprising:
a device comprising:
a drug delivery catheter having a proximal end and a distal end, said drug delivery catheter having a penetrating drug delivery element disposed on the distal end and a drug delivery lumen extending from the proximal end to the distal end of said drug delivery catheter;
an occluding mechanism disposed about the drug delivery catheter a short distance proximal to the penetrating element, said occluding mechanism adapted to occlude the ostium of the coronary sinus when placed in proximity thereto; and
a reservoir; and
a potentially embolic therapeutic agent comprising an implantable matrix comprising fibrin glue contained within the reservoir, said reservoir in communication with the drug delivery lumen.

23. A system for treating the heart by injecting therapeutic agents into a target site within the coronary venous system, said system comprising:
a device comprising:
a drug delivery catheter having a proximal end and a distal end, said drug delivery catheter having a penetrating drug delivery element disposed on the distal end and a drug delivery lumen extending from the proximal end to the distal end of said drug delivery catheter;
an occluding mechanism disposed about the drug delivery catheter a short distance proximal to the penetrating element, said occluding mechanism adapted to occlude the ostium of the coronary sinus when placed in proximity thereto; and
a reservoir; and
a potentially embolic therapeutic agent comprising an implantable controlled release matrix comprising microspheres contained within the reservoir, said reservoir in communication with the drug delivery lumen.

24. A system for treating the heart by injecting therapeutic agents into a target site within the coronary venous system, said system comprising:
a device comprising:
a drug delivery catheter having a proximal end and a distal end, said drug delivery catheter having a penetrating drug delivery element disposed on the distal end and a drug delivery lumen extending from the proximal end to the distal end of said drug delivery catheter;
a guide catheter slidably disposed about the drug delivery catheter, said guide catheter having a proximal end and a distal end, said distal end of the guide catheter adapted for insertion into the coronary sinus;
an occluding mechanism disposed about the guide catheter, said occluding mechanism adapted to occlude the ostium of the coronary sinus; and
a reservoir; and
a potentially embolic therapeutic agent comprising an implantable controlled release matrix comprising a polymeric matrix contained within the reservoir, said reservoir in communication with the drug delivery lumen.

25. A system for treating the heart by injecting therapeutic agents into a target site within the coronary venous system, said system comprising:
a device comprising:
a drug delivery catheter having a proximal end and a distal end, said drug delivery catheter having a penetrating drug delivery element disposed on the distal end and a drug delivery lumen extending from the proximal end to the distal end of said drug delivery catheter;

a guide catheter slidably disposed about the drug delivery catheter, said guide catheter having a proximal end and a distal end, said distal end of the guide catheter adapted for insertion into the coronary sinus;

an occluding mechanism disposed about the guide catheter, said occluding mechanism adapted to occlude the ostium of the coronary sinus; and a reservoir; and a potentially embolic therapeutic agent comprising an implantable controlled release matrix comprising a hydrogel contained within the reservoir, said reservoir in communication with the drug delivery lumen.

26. A system for treating the heart by injecting therapeutic agents into a target site within the coronary venous system, said system comprising:

a device comprising:

a drug delivery catheter having a proximal end and a distal end, said drug delivery catheter having a penetrating drug delivery element disposed on the distal end and a drug delivery lumen extending from the proximal end to the distal end of said drug delivery catheter;

a guide catheter slidably disposed about the drug delivery catheter, said guide catheter having a proximal end and a distal end, said distal end of the guide catheter adapted for insertion into the coronary sinus;

an occluding mechanism disposed about the guide catheter, said occluding mechanism adapted to occlude the ostium of the coronary sinus; and a reservoir; and a potentially embolic therapeutic agent comprising an implantable controlled release matrix comprising fibrin glue contained within the reservoir, said reservoir in communication with the drug delivery lumen.

27. A system for treating the heart by injecting therapeutic agents into a target site within the coronary venous system, said system comprising:

a device comprising:

a drug delivery catheter having a proximal end and a distal end, said drug delivery catheter having a penetrating drug delivery element disposed on the distal end and a drug delivery lumen extending from the proximal end to the distal end of said drug delivery catheter;

a guide catheter slidably disposed about the drug delivery catheter, said guide catheter having a proximal end and a distal end, said distal end of the guide catheter adapted for insertion into the coronary sinus;

an occluding mechanism disposed about the guide catheter, said occluding mechanism adapted to occlude the ostium of the coronary sinus; and a reservoir; and a potentially embolic therapeutic agent comprising an implantable controlled release matrix comprising microspheres contained within the reservoir, said reservoir in communication with the drug delivery lumen.

* * * * *